(12) United States Patent
Stefanoff (10) Patent No.: US 12,109,146 B1
(45) Date of Patent: Oct. 8, 2024

(54) FLUID THERMAL MANAGEMENT STORAGE APPARATUSES AND METHODS

(71) Applicant: Buddy Stefanoff, Owasso, OK (US)

(72) Inventor: Buddy Stefanoff, Owasso, OK (US)

( * ) Notice: Subject to any disclaimer, the term of this patent is extended or adjusted under 35 U.S.C. 154(b) by 682 days.

(21) Appl. No.: 16/883,198

(22) Filed: May 26, 2020

Related U.S. Application Data (60) Provisional application No. 62/853,136, filed on May 27, 2019.

(51) Int. Cl.
*A61F 7/00* (2006.01)

(52) U.S. Cl.
CPC ............ *A61F 7/007* (2013.01); *A61F 7/0085* (2013.01); *A61F 2007/0076* (2013.01); *A61F 2007/0093* (2013.01); *A61F 2007/0096* (2013.01)

(58) Field of Classification Search
CPC .................... A61F 7/007; A61F 7/0085; A61F 2007/0076; A61F 2007/0093
See application file for complete search history.

(56) References Cited

U.S. PATENT DOCUMENTS

| | | | | |
|---|---|---|---|---|
| 2005/0109040 | A1* | 5/2005 | Hansen | A47F 3/0482 62/3.6 |
| 2014/0352329 | A1* | 12/2014 | Bloedow | F25D 3/06 62/3.6 |
| 2018/0051918 | A1* | 2/2018 | VanTubergen, Jr. | F25B 27/002 |

* cited by examiner

*Primary Examiner* — Tigist S Demie (57) ABSTRACT

Fluid thermal management storage apparatuses and methods are disclosed herein. An example apparatus can include a dewar vessel having a heatsink mounted thereon. The dewar vessel can be configured to receive and retain a bag of whole blood. A thermoelectric sub-assembly is mounted to the heatsink, where the thermoelectric sub-assembly includes a solid-state thermoelectric element, a fan disposed below the solid-state thermoelectric element for circulating air within the dewar vessel, and a controller having a processor and memory. The processor executes instructions to maintain the bag of whole blood at a safe operational temperature for a period of time.

16 Claims, 4 Drawing Sheets

FLUID THERMAL MANAGEMENT STORAGE APPARATUSES AND METHODS

CROSS-REFERENCE TO RELATED APPLICATION(S)

This non-provisional application claims the benefit and priority of U.S. patent application Ser. No. 62/853,136, titled "FLUID THERMAL MANAGEMENT STORAGE APPARATUSES AND METHODS", filed on May 27, 2019, which is hereby incorporated by reference herein in its entirety, including all references and appendices cited therein, for all purposes, as if fully set forth herein.

TECHNICAL FIELD

The present disclosure relates to fluid cooling and storage, and in more specifically, but not by way of limitation, to systems and methods that allow for thermal management, storage, and transportation of fluids. Some embodiments allow for transportation of biomedical products such as blood products or tissue.

BRIEF DESCRIPTION OF THE DRAWINGS

The detailed description is set forth with reference to the accompanying drawings. The use of the same reference numerals may indicate similar or identical items. Various embodiments may utilize elements and/or components other than those illustrated in the drawings, and some elements and/or components may not be present in various embodiments. Elements and/or components in the figures are not necessarily drawn to scale. Throughout this disclosure, depending on the context, singular and plural terminology may be used interchangeably.

DETAILED DESCRIPTION

Overview

Whole blood is the medically preferred transfusing agent for treating blood loss. During periods of active blood loss, most current treatments involve delivering blood products. The problem with blood products is that they cannot individually deliver the full spectrum of care delivered by whole blood: fibrinogenic effect in support of the coagulation cascade, volume expansion to increase blood pressure, and oxygen distribution to treat hypoxemia. Even if a patient is revived and delivered to appropriate care, many adverse health effects can still be realized by the patient. Periods during blood loss, when the body is transporting anaerobic blood, can lead to brain and tissue compromise. Immediate medical care in combination with whole blood transfusions will save lives.

Time is a fundamental factor in the effectiveness of medical care. The time taken until the receipt of appropriate medical intervention will affect the general outcome of medical care, including the risk of death, the speed of recovery and the level of residual disability. Therefore, the allocation of medical resources has to ensure the timely provision of medical care. Trained non-medical first responders, capable of providing emergency life-saving procedures as soon as possible within ten minutes after injury, will help to improve treatment outcomes and save live. A complement to timely medical care is the appropriate interventional tools and treatments. Although acknowledged as efficacious, delivering fresh whole blood to the point of injury is logistically difficult. Temperature regulation is one of the biggest hurdles in allowing this capability. Although there is no known universal blood type, Low Titer Type O whole blood is shown to be the acceptable universal resuscitation product for hemorrhagic shock.

Current methods for transporting blood are ineffective and potentially dangerous. Use of the "golden hour cooler" creates instances where blood is cooled beyond safe levels and has caused hemolysis in areas of the blood bag that freeze during contact with the transport device. Additionally, once introduced into the cooler, the blood cannot safely be re-introduced into inventory. Blood products (plasma, packed red blood cells, platelet concentrates etc.) are made from whole blood. Each blood component serves a unique, medically efficacious role, but cannot deliver all the health benefits derived from the administration of whole blood. Additionally, separating blood into its component parts is time consuming and costly. Blood components present similar logistical and delivery problems as those related to whole blood. Often a single patient is required to receive blood components in a 1:1, or 1:1:1 ratio. Each 1: represents a blood component part that must be carted to the point of transfusion, require similar cold chain of custody and data logging requirements.

The devices, systems, and methods disclosed herein extend the availability of delivering whole blood from a fixed storage area to the point of injury. Whole blood is the medically preferred agent for transfusing. However, blood transportation requires a sophisticated range of logistical protocols and materiel handling procedures to ensure that it is safe for use in patients. From the point of collection, to testing and processing in the lab, during transportation to and storage in medical treatment facilities and onward to eventual transfusion into a patient, blood is carefully logged and tracked.

However, there is an identified gap in available technology that allows medics to bring whole blood, particularly while blood is being carried by a person in a dynamic environment. There is also a gap in practical application of electronic documentation and record keeping to portable blood storage and delivery/use.

Exsanguination is a leading cause of battlefield death. Some guidelines prescribe resuscitation fluids of choice for patients in hemorrhagic shock, listed from most to least preferred, as: whole blood; plasma, red blood cells (RBCs) and platelets in a 1:1:1 ratio*; plasma and RBCs in a 1:1 ratio; plasma or RBCs alone; Hextend; and crystalloid (Lactated Ringer's or Plasma-Lyte A). Whole blood is typically forsaken for blood products due to the complexity and custody issues surrounding the cartage of whole blood. Currently products made from whole blood are carted to the point of injury. The process of separating blood into its component parts is time consuming and technically sophisticated. Each component of blood serves a medicinal function but when administered individually cannot deliver the required treatment effect. When whole blood is not available, as seen above, current doctrine prescribes delivering blood components in a 1:1:1, or 1:1 ratio. The time to administer the blood products, and volume to be carted, are reduced by using whole blood. The technical and logistical complexities required to deliver these products can be reduced by the ability to deliver whole blood. Further benefit to this proposition is realized because the whole blood being used is from the blood bank, therefore it is FDA compliant. It will be understood that low titer Type O blood shows an approximate 1 in 10,000 risk of side effects. These side effects can readily be medically managed in the field.

The systems and methods disclosed herein pertain to a holistic approach to the challenge presented by attempting to safely deliver fresh whole blood from theater medical stores with succession to the point of injury, while maintaining cold chain of custody, data chain of custody and integration in various systems.

Theater blood operation support functions are closely coupled with clinical services to ensure the total life cycle tracking of blood products from the point of origin/donor ultimately to the transfused patient or point of destruction. In the operational environment however, the blood community often works in medical support facilities characterized by disconnected, intermittent, and/or low-bandwidth (DIL) network connectivity. Thus, there is a requirement for a solution that allows for the capture of data in an offline mode, and for the subsequent synchronization of that data with the enterprise blood store once connectivity is restored.

In some embodiments, the thermo-electric cooling (TEC) devices, systems, and methods disclosed herein include fully integrated communication and control electronics that allow extended temperature regulation of the device when, cooling demand is powered exclusively by a power source, via cycling and insulative capacity of the devices with projected increase in mean time between failures versus mechanical cooling mechanisms.

An example embodiment of a device of the present disclosure comprises a 0.80 liter stainless steel dewar equipped with a solid state multistage TEC module, which allow for operating temperatures well below requirements for whole blood storage while consuming only six Watts of power. Some embodiments may have different volumetric sizing and consume more or less power that the embodiment described.

With no moving parts to fail, the devices of the present disclosure are highly ruggedized. Existing compressor technology presents challenges related to compressor orientation, flammability of compressor gases, component fragility, operational service life when powered by batteries only, and function in a humid/wet environment. The devices of the present disclosure overcome these potential compressor cooling system faults using solid state technology. The components used to in the devices of the present disclosure do not require a specified orientation for operation, do not contain flammable gases, are shock hardened via solid-state components, have built in protections for catastrophic battery failure, and are water-resistant.

Units of varying sizes can be created, but with in-common electronics, controls and materials. Some embodiments utilize thermo-electric cooling to ensure the ruggedization of the units in combat, austere, or generally unwelcoming environments.

The devices, systems, and methods disclosed herein provide for a blood delivery system of systems that will allow safe and controlled movement of fresh whole blood from initial storage to the point of injury using three form factors: large, medium, and small devices. A consistent technical approach for these various form factors is maintained with respect to cooling, power, and data regulation, with scaling of the technology to satisfy the increases in demand for power, data, and temperature regulation that will occur as we move from the small to the large unit requirements. The present disclosure describes regulation of temperature state, log and delivers pertinent data about the blood and transfusion activity. Integrating temperature regulation via solid state thermo-electric heat pump technology via peltier devices eliminates the needs for separate heating and cooling systems, which also increases the mean time between failures and lower the energy consumption versus systems using compressors for their cooling.

With respect to sizing, a large device receives its blood inventory from an existing warehouse blood stores and houses approximately 40 bags of blood that can be moved to from location to location. The medium unit, housing approximately four bags of blood, is stocked with blood taken from the large unit and will be transported further into other operating areas and serve as ready for transfusion at the temporary medical staging area, or a single bag of blood can be used to stock the small device, which can then be carried directly to the point of injury for transfusing at that point.

Blood is a pathogen so each unit has been designed such that blood storage wells can be cleaned and sanitized should they become contaminated. An example device can include an energy management sub-assembly will include safety features such as fuses and fail-safes to protect users from inadvertent failures. The device can also be designed to harvest energy from limited sources, such as portable solar panels, and will provide rapid availability of electrical power as well as charging of the battery. Various aspects related to small whole blood delivery systems can be scaled up and utilized for the medium and large scale delivery systems, and offers the benefits of ruggedness, reliability, commonality of components and ease of maintenance.

A larger transportation system can include a rolling, large, portable whole blood storage system that is capable of housing approximately 40 bags of whole blood, with succession to our hand portable, medium, whole blood storage system that is capable of housing approximately four bags of whole blood, with further succession to a portable, small, whole blood storage system that is capable of housing one bag of fresh whole blood.

As noted above system-of-systems involves three different sized blood storage embodiments (e.g., small, medium, large). All three systems share the same conceptual technologies that can be scaled for performance at the different sizes. Each of these embodiments for whole blood storage systems include persistent integrated data logging to ensure cold chain compliance, data chain compliance, and state of blood efficacy. At all times in the system-of-systems the blood is temperature regulated, data regulated and classified for safe use. Should the blood be transported but not used it can reliably be re-stored until it reaches the end of its serviceable life.

The cold chain of custody is data logged and will let a user know if the blood has been maintained at appropriate temperatures. Important data points for blood include storage temperature throughout succession, expiration date, and information at the point of transfusion. Ruggedization is another important factor in the deployment of our system. As noted above, a solid state multistage solid-state thermo-electric cooling module is employed for temperature regulation, freedom of device orientation, extended life cycle and superior power delivery and charging options, programmable micro-controllers for power management, temperature regulation and data logging, passive and active thermal management in the form of heat sinks, bar code scanning for safe data logging of blood information, and insulative materials to increase the blood holdover times, multiple power inputs to include AC respecting wave form variations across operating environments, and DC to include batteries and solar power inputs for each device size.

Example devices can include components that comprise, but are not limited to, a power storage device that provides sufficient power density for the required period of operation with fail-safes; a micro-controller with micro-controller programming that manages sensor, thermal, and power demands while providing constant monitoring on the temperature state and data-logging within the vessel with ability to deliver data back to the systems. Some embodiments comprise a solid state, multistage thermo-electric cooling/heating module for energy efficient temperature control and precise regulation. One or more embodiments may be ruggedized, and include water-proof/water-resistant housings to include the development of vacuum insulated dewar flasks constructed with medical grade SAE 316 stainless steel. Example devices integrate multiple power input capabilities to include AC (alternating current), DC (direct current) and DC solar.

In sum, the present disclosure pertains to devices, systems, and methods for storage and transportation of fluids, such as blood or blood products in a thermally managed state. In some embodiments, the systems and methods disclosed herein comprise self-contained units that receive a unit of blood. A temperature of the blood can be lowered from an ambient temperature to a safe storage temperature range, maintained at this safe storage temperature range, and warmed to a transfusion temperature range. In various embodiments, the blood can be maintained at the safe storage temperature range for time frames that include 24, 36, and 48 hours using a thermal management system. In some embodiments, a device or apparatus disclosed herein incorporate a thermal management system that lacks moving parts, has a compact size, provides precise temperature control, as well as provides ruggedness and reliability.

Illustrative Embodiments

Figure 1:
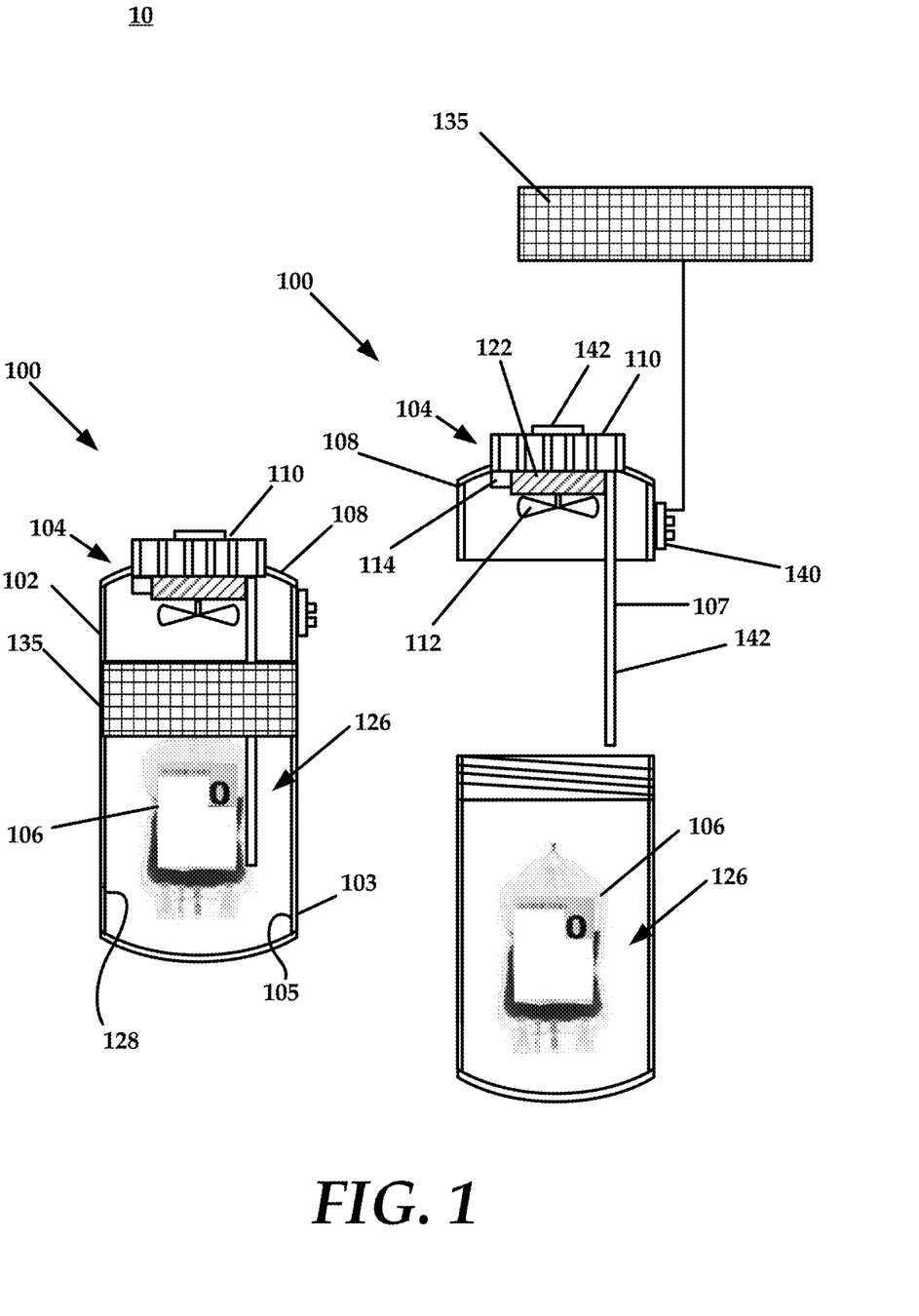
FIG. 1 depicts an illustrative architecture in which techniques and structures for providing the systems and methods disclosed herein may be implemented.

Turning now to the drawings, FIG. 1 depicts an illustrative architecture 10 in which techniques and structures of the present disclosure may be implemented. The illustrative architecture 10 may include an example blood transportation apparatus 100 that includes a vessel 102 and a thermal management system 104.

According to some embodiments, the vessel 102 comprises an insulated enclosure that receives a unit of blood 106. The unit of blood 106 can comprise whole blood or fractionated blood product such as plasma. The blood is typically stored inside a polymeric bag. In one example embodiment, the vessel 102 comprises an insulated vessel such as a dewar or other similar vacuum flask having an outer shell 103 and an inner shell 105 that are separated from one another. A vacuum can be induced in the separation between the outer shell 103 and the inner shell 105 to reduce thermal transfer from inside the vessel 102 to the ambient environment, and vice-versa.

In one or more embodiments, the vessel 102 forms a first portion of the apparatus 100 and the thermal management system 104 forms a second portion of the apparatus 100. The thermal management system 104 and the vessel 102 can be configured to couple with one another to provide a hermetic seal therebetween. In one example, the thermal management system 104 is integrated into a cap or top 108 that threadably couples with a terminal end of the vessel 102. In another example embodiment, a seal such as an o-ring or gasket can be positioned on either or both of the terminal end of the vessel 102 or the cap or top 108. When the vessel 102 and the cap or top 108 are coupled, the gasket(s) create a sealed connection therebetween. In some embodiments, the cap or top 108 can be press fit onto the vessel 102.

In various embodiments, the unit of blood 106 can be placed within the vessel 102 in various thermal states. For example, the unit of blood 106 can be placed into the vessel 102 in a pre-chilled state where the unit of blood 106 is already at a preferred safe storage temperature. The preferred safe storage temperature can be within a specified range of temperatures of approximately 1° Celsius to approximately 4° Celsius, inclusive. In other embodiments, the unit of blood 106 can be at an ambient temperature and will be brought to within the range of preferred safe storage temperatures disclosed above.

According to some embodiments, the thermal management system 104 can comprise a heat sink 110, a fan 112, a microcontroller (or generally "controller") 114, a thermoelectric sub-assembly 116, and a power management sub-assembly 118. In various embodiments, the heat sink 110 can comprise a radial fin element heat sink that includes a core with a plurality of fins extending therefrom. In one or more embodiments, the heat sink 110 is mounted to the cap or top 108 such that it extends externally to the vessel 102. In another embodiment, the heat sink 110 coupled to a thermal heat pipe 107 that extends externally into the vessel 102 when the cap or top 108 is joined to the vessel 102.

The microcontroller 114 can be mounted on a PCB (printed circuit board) that is fixed onto an underside of the heat sink 110. The microcontroller 114 can advantageously be located anywhere on or inside the apparatus 100.

In some embodiments, the thermoelectric sub-assembly 116 comprises a thermoelectric element 122 and a thermocouple 124. The thermoelectric element 122 can comprise, for example, a peltier junction or other similar solid-state thermoelectric element. In some embodiments, the thermoelectric element 122 is a multistage thermoelectric element that provides significantly higher temperature differentials than those obtained with single stage devices. Multi-stage TECs are suitable for low temperature applications where a moderate cooling capacity is required.

In some embodiments the thermoelectric element 122 is installed on the PCB. The thermocouple 124 senses a temperature (current operational temperature) within the apparatus 100 and relays signals indicative of the temperature to the microcontroller 114. Generally, the microcontroller 114 selectively adjusts a temperature within the vessel 102 of the apparatus 100 based on signals received from the thermocouple 124. This selective adjustment of temperature can involve the microcontroller 114 controlling operations of the thermoelectric element 122.

In some embodiments, the fan 112 is mounted below the thermoelectric element 122 such that the thermoelectric element 122 is placed between the underside of the heat sink 110 and the fan 112. In one or more embodiments, the fan 112 can be used to increase or enhance convective thermal transfer within the vessel 102 around the unit of blood 106. For example, the fan 112 circulates air within an airspace 126 or gap between the unit of blood 106 and an inner surface 128 of the vessel 102. In some embodiments, the airspace 126 is minimized to reduce an fluid volume around the unit of blood 106. Air moved by the fan 112 travels across an outer surface of the unit of blood 106 so as to enhance thermal transfer of heat to or from the unit of blood 106 based on operation of the thermoelectric element 122. To be sure, the thermoelectric element 122 includes both heating and cooling surfaces. Thus, the thermoelectric element 122 can be used to heat or cool the inside of the vessel 100 as needed. Additional aspects of the use of the thermoelectric element 122 to heat or cool the vessel 102 are disclosed infra.

In various embodiments, the power management sub-assembly 118 can include an energy storage device 130 and a power source 132. In various embodiments, the energy storage device 130 and power source 132 can be integrated into a single element, such as a replaceable battery. In other embodiments, the energy storage device 130 could include a hybrid energy storage device that comprises both electric field energy storage elements and electrochemical energy storage elements. The use of a hybrid energy storage device allows for long-term operation without use of the power source 132. To be sure, the hybrid energy storage device can be recharged using the power source 132 as desired, but in various embodiments, embodiments of the apparatus 100 that include a hybrid energy storage device can operate to sustain a temperature of the unit of blood at a safe storage temperature range for time frames that include 24, 36, and 48 hours without requiring the hybrid energy storage device to be recharged. The power management sub-assembly 118 can be controlled using the microcontroller to maintain the bag of whole blood at a safe operational temperature for a period of time.

In some embodiments, the external power source 132 can comprise a photovoltaic member that is used to charge the energy storage device 130. The photovoltaic member could comprise a plurality of photovoltaic cells that are disposed around an outer surface of the vessel 102. In other embodiments, the PCB can include a connector that allows for an external power source 134 to be utilized in addition to, or in lieu of the power source 132. The external power source 134 could include a photovoltaic cell mat 135 as an example.

In some instances, the apparatus 100 comprises an electrical interface 140 that provides electrical coupling between the external power source 134 and the energy storage device of the apparatus 100. As described infra, the electrical interface 140 can also couple the apparatus 100 to another blood storage apparatus in a system-of-systems. The electrical interface 140 can also comprise an outward facing switch or other similar element that can allow a user to toggle the apparatus on and off, or from a cooling mode to a heating mode. In some instances, a first switch is included that is used to toggle the device between on/off. In some instances, a second switch is included that is used to toggle the device between cooling mode/heating mode.

The thermal management within the apparatus 100 can be controlled using the microcontroller 114. In general, the microcontroller 114 comprises a processor and memory. The memory stores control logic that can be executed by the microcontroller 114 to control operations of the elements disclosed herein. The microcontroller 114 can be configured to provide modes of operation in some embodiments. For example, the microcontroller 114 can provide a chill mode, a maintenance mode, and/or a warming mode. A chill mode includes instances where the unit of blood 106 requires chilling to bring a temperature of the unit of blood 106 down to a safe storage temperature range. This chill mode can also be utilized to bring a temperature within the vessel 102 to within a safe storage temperature range prior to introducing the unit of blood 106 therein. The maintenance mode is utilized when the temperature within the vessel 102, with the unit of blood 106 present therein is within a safe storage temperature range. The warming mode is utilized when the unit of blood 106 is needed. The microcontroller 114 can evenly and effectively warm the unit of blood 106 to use, for example, in a transfusion process. Each of these modes can be selected by a user through an interface provided on the apparatus 100 itself or can be controllable wirelessly through an application.

Thus, apparatus 100 can comprise a communications interface 136 that allows the microcontroller 114 to transmit and/or receive data over a network connection. The network connection can include cable networks, the Internet, wireless networks, and other private and/or public networks. In some instances, the network connection may include cellular, Wi-Fi, or Wi-Fi direct, or a short-range wireless connection such as NFC, Bluetooth, and the like. This allows for remote temperature monitoring, control, and data logging of apparatus temperatures. In various embodiments, these data (and direct control of the apparatus 100) can be accessed and stored by a server or cloud 138. In other embodiments, the apparatus 100 can be controlled and monitored using an application executing on a mobile device.

Generally, the microcontroller 114 can receive temperature signals from the thermocouple 124 that indicate a temperature within the vessel 102. When the unit of blood 106 is present in the apparatus 100 a temperature within the vessel 102 can be assumed to be a temperature of the unit of blood 106. Depending on the desired mode of operation, the microcontroller 114 can control the use of the thermoelectric cooling sub-assembly 116 to selectively adjust a temperature within the vessel 102. For example, to decrease a temperature within the vessel 102, the microcontroller 114 can activate a cooling surface of the thermoelectric element 122. The microcontroller 114 can also activate the fan 112 if needed. To decrease a temperature within the vessel 102, the microcontroller 114 can activate a heating surface of the thermoelectric element 122. The microcontroller 114 can also activate the fan 112 if needed. When the temperature within the vessel 102 is a safe storage temperature range the microcontroller 114 can selectively and periodically cycle the thermoelectric cooling sub-assembly 116 to cool the vessel 102 utilizing pulse width modulation. This process ensures that the energy is drawn from the power management sub-assembly 118 only when needed to ensure that the temperature within the vessel 102 is within the safe storage temperature range.

In some embodiments, the apparatus 100 can comprise a thermal dispersion member 142 that can couple to either or both of the thermoelectric element 122 and/or the heat sink 110. The thermal dispersion member 142 could include an elongated tube or other similar element that conducts heat into, and out of, the vessel 102. It will be understood that the thermal dispersion member 142 may be constructed so as to not damage or perforate the unit of blood 106. Thus, the thermal dispersion member 142 can have a rounded or coated terminal end. The size and/or shape of the thermal dispersion member 142 can vary according to the shape and/or size of the vessel.

Also, while the thermal management system 104 has been disclosed as being associated with the cap 108 of the apparatus 100, the thermal management system 104 can be located at any position on the apparatus 100, including the sidewall of the vessel 102 or a bottom of the vessel 102, as an example.

In one example embodiment, an example apparatus (such as the example blood transportation apparatus of FIG. 1) comprises a stainless steel dewar with a high vacuum of 10-3 to 10-7 mbar and internal dimensions of 50 mm by 20 mm by 10 mm, which provides a volume of one liter. If the maximum ambient temperature anticipated is 54° C., then a 20 watt, multistage TEC with a dimensional profile of 30 mm by 30 mm by 6.7 mm, will attain a maximum temperature differential between a hot (Th) side and a cold (Tc) side of the multistage TEC of approximately 105 C (Tmax). This is sufficient to maintain an internal temperature of the apparatus 100 to within approximately two to four degrees Celsius within the one liter stainless steel dewar, regardless of vessel orientation. As the thermal conductivity of the dewar is 0001 W/m° C., the advanced energy management and precise temperature controls disclosed herein can cycle the multistage TEC on and off utilizing pulse width modulation and provide a 24 hour stand-alone operational capability.

Figure 2:
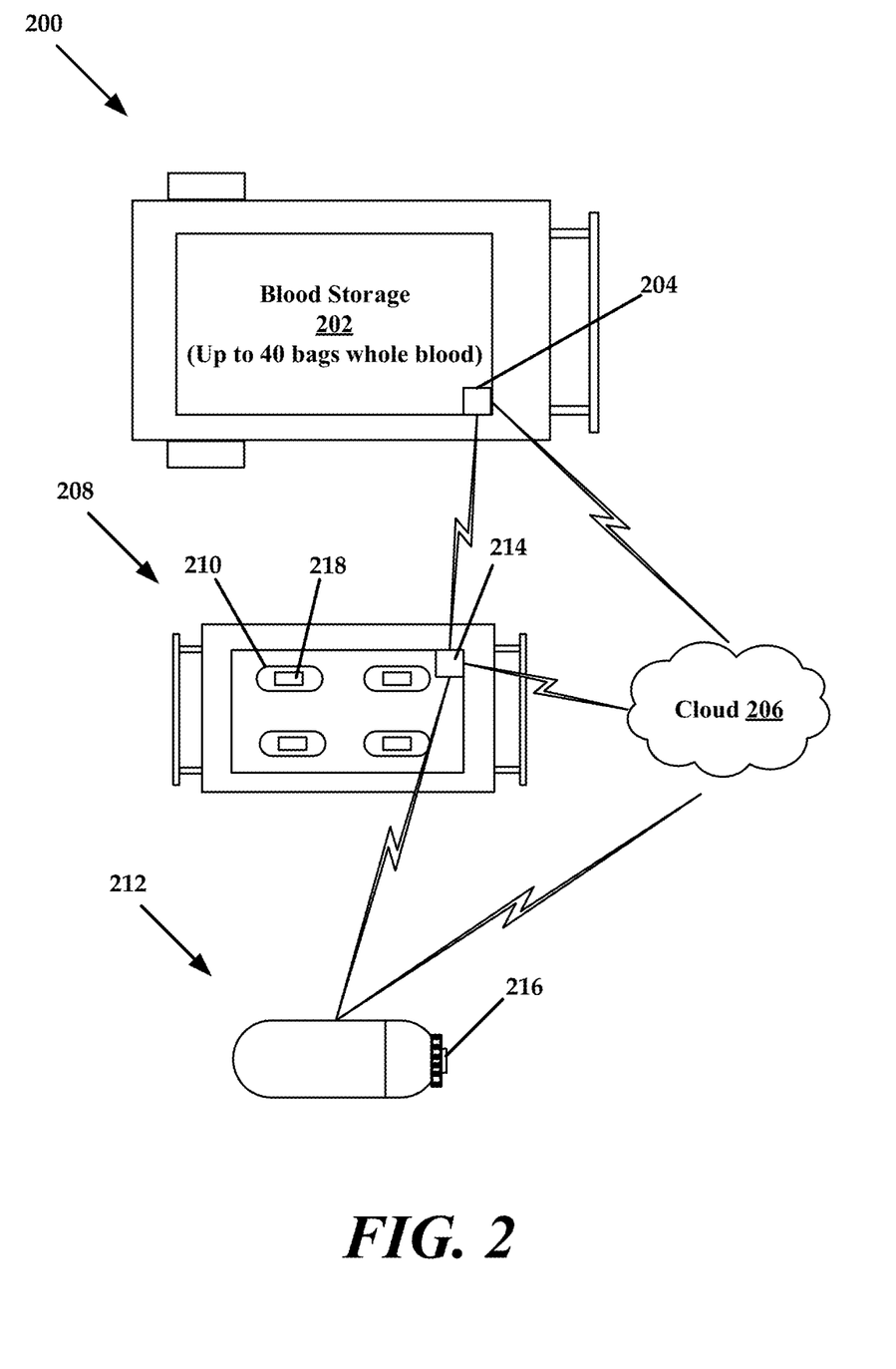
FIG. 2 is a schematic diagram of an example system-of-systems, constructed in accordance with the present disclosure.

A SoS interface 144 can be used to communicatively and electrically interface the apparatus 200 with another, larger apparatus in a system-of-systems configuration, as best illustrated in FIG. 2. In FIG. 2, a large-scale, portable blood apparatus 200 can be used to store and transport up to 40 bags of whole blood in a blood storage area 202. The large-scale, portable blood apparatus 200 can have wheels, or other means of conveyance. In some embodiments, the large-scale, portable blood apparatus 200 can include a controller 204 that provides temperature control and data logging capabilities as disclosed herein. The controller 204 can comprise a processor and memory for storing instructions, as well as a communications interface for transmitting data to a cloud 206, or directly to other devices such as a medium-scale, portable blood apparatus 208, or a small-scale, portable blood apparatus 210. In some instances, the devices of the system-of-systems configuration may communicate over cellular, Wi-Fi, or Wi-Fi direct, or a short-range wireless connection such as NFC, Bluetooth, and the like. Any short-range or long-range communications protocol can be used.

The medium-scale, portable blood apparatus 208 can comprise docking ports, such as docking port 218 that include a receiving interface 212. The receiving interface can allow for both electrical and communicatively coupling with the small-scale, portable blood apparatus 210. The medium-scale, portable blood apparatus 208 can also comprise a controller 214 that provides temperature control and data logging capabilities as disclosed herein. The controller 204 can comprise a processor and memory for storing instructions, as well as a communications interface for transmitting data to a cloud 206, or directly to other devices such as a large-scale, portable blood apparatus 200, or a small-scale, portable blood apparatus 210.

The small-scale, portable blood apparatus 210 can include the apparatus 100 of FIG. 1. An interface 216 (corresponding to the SoS interface 144 of FIG. 1), can communicatively and electrically couple with the receiving interface 212 of the medium-scale, portable blood apparatus 208. When the small-scale, portable blood apparatus 210 is docked with the medium-scale, portable blood apparatus 208, the medium-scale, portable blood apparatus 208 can provide power to the small-scale, portable blood apparatus 210 to cool the blood bag inside the small-scale, portable blood apparatus 210. When the small-scale, portable blood apparatus 210 is removed from the docking port 218 of the medium-scale, portable blood apparatus 208, the controller of the small-scale, portable blood apparatus 210 can automatically switch to a self-contained and self-directed mode where the small-scale, portable blood apparatus 210 controls thermal management of the blood bag inside the small-scale, portable blood apparatus 210. When the small-scale, portable blood apparatus 210 is returned to the docking port 218, the small-scale, portable blood apparatus 210 can transfer data that was logged during its use in the self-contained and self-directed mode. Again, the small-scale, portable blood apparatus 210 can be configured to operate in a synchronous or real-time manner as well, transferring logged data about vessel temperature to any component of the system-of-systems.

Any and/or all elements, as disclosed herein, can be formed from a same, structurally continuous piece, such as being unitary, and/or be separately manufactured and/or connected, such as being an assembly and/or modules. Any and/or all elements, as disclosed herein, can be manufactured via any manufacturing processes, whether additive manufacturing, subtractive manufacturing and/or other any other types of manufacturing. For example, some manufacturing processes include three dimensional (3D) printing, laser cutting, computer numerical control (CNC) routing, milling, pressing, stamping, vacuum forming, hydroforming, injection molding, lithography and/or others.

Any and/or all elements, as disclosed herein, can include, whether partially and/or fully, a solid, including a metal, a mineral, a ceramic, an amorphous solid, such as glass, a glass ceramic, an organic solid, such as wood and/or a polymer, such as rubber, a composite material, a semiconductor, a nano-material, a biomaterial and/or any combinations thereof. Any and/or all elements, as disclosed herein, can include, whether partially and/or fully, a coating, including an informational coating, such as ink, an adhesive coating, a melt-adhesive coating, such as vacuum seal and/or heat seal, a release coating, such as tape liner, a low surface energy coating, an optical coating, such as for tint, color, hue, saturation, tone, shade, transparency, translucency, non-transparency, luminescence, anti-reflection and/or holographic, a photo-sensitive coating, an electronic and/or thermal property coating, such as for passivity, insulation, resistance or conduction, a magnetic coating, a water-resistant and/or waterproof coating, a scent coating and/or any combinations thereof.

Figure 3:
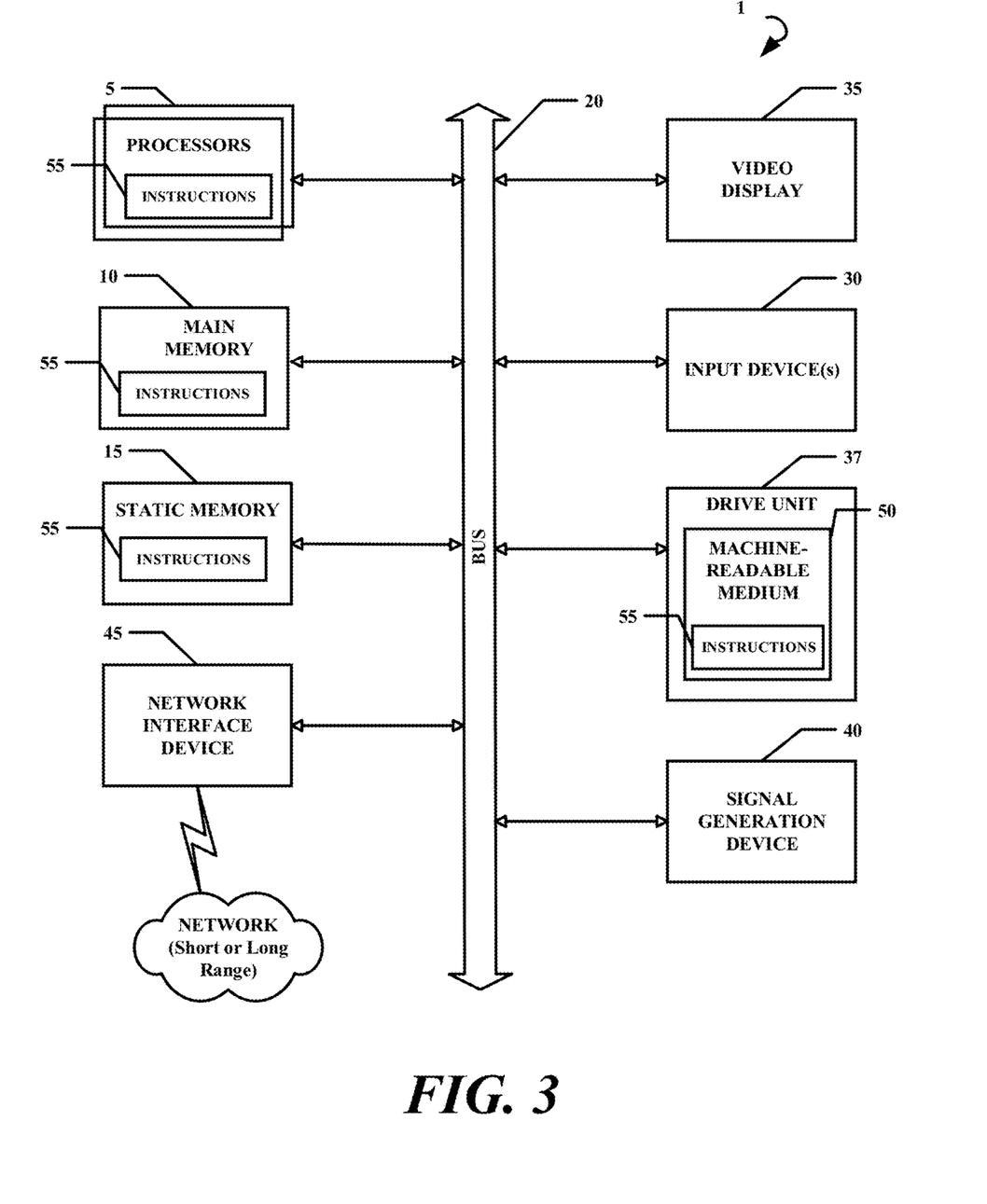
FIG. 3 is a schematic diagram of an example computer system that can be used in accordance with the present disclosure.

FIG. 3 is a diagrammatic representation of an example machine in the form of a computer system 1, within which a set of instructions for causing the machine to perform any one or more of the methodologies discussed herein may be executed. In various example embodiments, the machine operates as a standalone device or may be connected (e.g., networked) to other machines. In a networked deployment, the machine may operate in the capacity of a server or a client machine in a server-client network environment, or as a peer machine in a peer-to-peer (or distributed) network environment. The machine may be a personal computer (PC), a tablet PC, a set-top box (STB), a personal digital assistant (PDA), a cellular telephone, a portable music player (e.g., a portable hard drive audio device such as a Moving Picture Experts Group Audio Layer 3 (MP3) player), a web appliance, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The computer system 1 includes a processor or multiple processor(s) 5 (e.g., a central processing unit (CPU), a graphics processing unit (GPU), or both), and a main memory 10 and static memory 15, which communicate with each other via a bus 20. The computer system 1 may further include a video display 35 (e.g., a liquid crystal display (LCD)). The computer system 1 may also include an alphanumeric input device(s) 30 (e.g., a keyboard), a cursor control device (e.g., a mouse), a voice recognition or biometric verification unit (not shown), a drive unit 37 (also referred to as disk drive unit), a signal generation device 40 (e.g., a speaker), and a network interface device 45. The computer system 1 may further include a data encryption module (not shown) to encrypt data.

The drive unit 37 includes a computer or machine-readable medium 50 on which is stored one or more sets of instructions and data structures (e.g., instructions 55) embodying or utilizing any one or more of the methodologies or functions described herein. The instructions 55 may also reside, completely or at least partially, within the main memory 10 and/or within the processor(s) 5 during execution thereof by the computer system 1. The main memory 10 and the processor(s) 5 may also constitute machine-readable media.

The instructions 55 may further be transmitted or received over a network via the network interface device 45 utilizing any one of a number of well-known transfer protocols (e.g., Hyper Text Transfer Protocol (HTTP)). While the machine-readable medium 50 is shown in an example embodiment to be a single medium, the term "computer-readable medium" should be taken to include a single medium or multiple media (e.g., a centralized or distributed database and/or associated caches and servers) that store the one or more sets of instructions. The term "computer-readable medium" shall also be taken to include any medium that is capable of storing, encoding, or carrying a set of instructions for execution by the machine and that causes the machine to perform any one or more of the methodologies of the present application, or that is capable of storing, encoding, or carrying data structures utilized by or associated with such a set of instructions. The term "computer-readable medium" shall accordingly be taken to include, but not be limited to, solid-state memories, optical and magnetic media, and carrier wave signals. Such media may also include, without limitation, hard disks, floppy disks, flash memory cards, digital video disks, random access memory (RAM), read only memory (ROM), and the like. The example embodiments described herein may be implemented in an operating environment comprising software installed on a computer, in hardware, or in a combination of software and hardware.

One skilled in the art will recognize that the Internet service may be configured to provide Internet access to one or more computing devices that are coupled to the Internet service, and that the computing devices may include one or more processors, buses, memory devices, display devices, input/output devices, and the like. Furthermore, those skilled in the art may appreciate that the Internet service may be coupled to one or more databases, repositories, servers, and the like, which may be utilized in order to implement any of the embodiments of the disclosure as described herein.

The corresponding structures, materials, acts, and equivalents of all means or step plus function elements in the claims below are intended to include any structure, material, or act for performing the function in combination with other claimed elements as specifically claimed. The description of the present technology has been presented for purposes of illustration and description, but is not intended to be exhaustive or limited to the present technology in the form disclosed. Many modifications and variations will be apparent to those of ordinary skill in the art without departing from the scope and spirit of the present technology. Exemplary embodiments were chosen and described in order to best explain the principles of the present technology and its practical application, and to enable others of ordinary skill in the art to understand the present technology for various embodiments with various modifications as are suited to the particular use contemplated.

If any disclosures are incorporated herein by reference and such incorporated disclosures conflict in part and/or in whole with the present disclosure, then to the extent of conflict, and/or broader disclosure, and/or broader definition of terms, the present disclosure controls. If such incorporated disclosures conflict in part and/or in whole with one another, then to the extent of conflict, the later-dated disclosure controls.

The terminology used herein can imply direct or indirect, full or partial, temporary or permanent, immediate or delayed, synchronous or asynchronous, action or inaction. For example, when an element is referred to as being "on," "connected" or "coupled" to another element, then the element can be directly on, connected or coupled to the other element and/or intervening elements may be present, including indirect and/or direct variants. In contrast, when an element is referred to as being "directly connected" or "directly coupled" to another element, there are no intervening elements present.

Although the terms first, second, etc. may be used herein to describe various elements, components, regions, layers and/or sections, these elements, components, regions, layers and/or sections should not necessarily be limited by such terms. These terms are only used to distinguish one element, component, region, layer or section from another element, component, region, layer or section. Thus, a first element, component, region, layer or section discussed below could be termed a second element, component, region, layer or section without departing from the teachings of the present disclosure.

The terminology used herein is for the purpose of describing particular embodiments only and is not intended to be necessarily limiting of the disclosure. As used herein, the singular forms "a," "an" and "the" are intended to include the plural forms as well, unless the context clearly indicates otherwise. The terms "comprises," "includes" and/or "comprising," "including" when used in this specification, specify the presence of stated features, integers, steps, operations, elements, and/or components, but do not preclude the presence or addition of one or more other features, integers, steps, operations, elements, components, and/or groups thereof.

Example embodiments of the present disclosure are described herein with reference to illustrations of idealized embodiments (and intermediate structures) of the present disclosure. As such, variations from the shapes of the illustrations as a result, for example, of manufacturing techniques and/or tolerances, are to be expected. Thus, the example embodiments of the present disclosure should not be construed as necessarily limited to the particular shapes of regions illustrated herein, but are to include deviations in shapes that result, for example, from manufacturing.

Aspects of the present technology are described above with reference to flowchart illustrations and/or block diagrams of methods, apparatus (systems) and computer program products according to embodiments of the present technology. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

In this description, for purposes of explanation and not limitation, specific details are set forth, such as particular embodiments, procedures, techniques, etc. in order to provide a thorough understanding of the present invention. However, it will be apparent to one skilled in the art that the present invention may be practiced in other embodiments that depart from these specific details.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" or "according to one embodiment" (or other phrases having similar import) at various places throughout this specification are not necessarily all referring to the same embodiment. Furthermore, the particular features, structures, or characteristics may be combined in any suitable manner in one or more embodiments. Furthermore, depending on the context of discussion herein, a singular term may include its plural forms and a plural term may include its singular form. Similarly, a hyphenated term (e.g., "on-demand") may be occasionally interchangeably used with its non-hyphenated version (e.g., "on demand"), a capitalized entry (e.g., "Software") may be interchangeably used with its non-capitalized version (e.g., "software"), a plural term may be indicated with or without an apostrophe (e.g., PE's or PEs), and an italicized term (e.g., "N+1") may be interchangeably used with its non-italicized version (e.g., "N+1"). Such occasional interchangeable uses shall not be considered inconsistent with each other.

Also, some embodiments may be described in terms of "means for" performing a task or set of tasks. It will be understood that a "means for" may be expressed herein in terms of a structure, such as a processor, a memory, an I/O device such as a camera, or combinations thereof. Alternatively, the "means for" may include an algorithm that is descriptive of a function or method step, while in yet other embodiments the "means for" is expressed in terms of a mathematical formula, prose, or as a flow chart or signal diagram.

That which is claimed is:

1. An apparatus comprising:
    a dewar vessel having a heatsink mounted to a lid of the dewar vessel, the dewar vessel being configured to receive and retain a bag of whole blood, the lid being releasably secured to the dewar vessel;
    a thermoelectric sub-assembly mounted to the heatsink, the thermoelectric sub-assembly comprising:
        a solid-state thermoelectric element;
        a fan disposed below the solid-state thermoelectric element for circulating air within the dewar vessel; and
    a controller comprising a processor and memory, the processor executing instructions to maintain the bag of whole blood at a safe operational temperature for a period of time.

2. The apparatus according to claim 1, further comprising a hybrid energy storage device that includes an electric field energy storage element and an electrochemical energy storage element.

3. The apparatus according to claim 1, wherein the processor is configured to log data comprising a temperature within the dewar vessel over the period of time.

4. The apparatus according to claim 3, further comprising a communications interface for transmitting the log data over a network.

5. The apparatus according to claim 3, further comprising a photovoltaic cell that is configured to wrap around an outer surface of the dewar vessel and unwrap from the dewar vessel when charging an energy storage device of the apparatus.

6. The apparatus according to claim 1, wherein the solid-state thermoelectric element is a Peltier junction.

7. The apparatus according to claim 1, further comprising a thermal dispersion member that is in thermal connectivity to the heatsink or the solid-state thermoelectric element, the thermal dispersion member transferring heat into or out of the dewar vessel based on an operational mode of the solid-state thermoelectric element.

8. The apparatus according to claim 1, further comprising a system-of-system interface for electrically and communicatively coupling with a system-of-systems component.

9. The apparatus according to claim 1, wherein the dewar vessel has two portions that include a vessel and the lid, the vessel and the cap being configured to create a hermetic seal when joined together.

10. The apparatus according to claim 1, further comprising a thermocouple disposed within the dewar vessel, the controller being configured to obtain a current operational temperature in real-time using the thermocouple.

11. The apparatus according to claim 1, wherein the apparatus is a small-scale, portable blood apparatus that is configured to dock with a medium-scale, portable blood apparatus.

12. The apparatus according to claim 11, wherein the medium-scale, portable blood apparatus controls the apparatus to maintain the safe operational temperature while the apparatus is docked with the medium-scale, portable blood apparatus.

13. The apparatus according to claim 11, wherein the controller causes the apparatus to automatically switch to maintaining the safe operational temperature when the apparatus is removed from docking with the medium-scale, portable blood apparatus.

14. The apparatus according to claim 13, wherein the docking comprises mating a system-of-system interface of the apparatus.

15. The apparatus according to claim 1, wherein the cap is threadably coupled to the dewar vessel.

16. The apparatus according to claim 1, wherein the thermoelectric sub-assembly is integrated into the cap.

* * * * *